(12) United States Patent
Licea Navarro et al.

(10) Patent No.: US 9,284,360 B2
(45) Date of Patent: Mar. 15, 2016

(54) DIAGNOSTIC TEST FOR INFECTIOUS DISEASES IN CATTLE

(71) Applicant: Centro de Investigacion Cientifica Y de Educacion Superior de Ensenada, Baja California (CICESE), Ensenada (MX)

(72) Inventors: Alexei Fedorovish Licea Navarro, Ensenada (MX); Jose Felix Olivares Quintero, Ensenada (MX); Ana Paola Gutierrez Ordonez, Ensenada (MX)

(73) Assignee: Centro de Investigacion Cientifica Y de Educacion Superior de Ensenada, Baja California (CICESE), Ensenada (MX)

( * ) Notice: Subject to any disclaimer, the term of this patent is extended or adjusted under 35 U.S.C. 154(b) by 0 days.

(21) Appl. No.: 14/380,863

(22) PCT Filed: Feb. 21, 2013

(86) PCT No.: PCT/MX2013/000025
§ 371 (c)(1),
(2) Date: Aug. 25, 2014

(87) PCT Pub. No.: WO2013/125936
PCT Pub. Date: Aug. 29, 2013

(65) Prior Publication Data
US 2015/0044689 A1    Feb. 12, 2015

(30) Foreign Application Priority Data
Feb. 24, 2012    (MX) .................... MX/a/2012/003180

(51) Int. Cl.
*A61K 38/00*    (2006.01)
*C07K 19/00*    (2006.01)
*C12N 15/62*    (2006.01)
*C07K 14/46*    (2006.01)
*G01N 33/569*    (2006.01)

(52) U.S. Cl.
CPC .............. *C07K 14/461* (2013.01); *C12N 15/62* (2013.01); *G01N 33/5695* (2013.01); *C07K 2319/00* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 6,982,085 B2 | 1/2006 | Andersen et al. | |
| 7,261,897 B2 | 8/2007 | Skeiky et al. | |
| 7,585,508 B1 | 9/2009 | Prendergast | |
| 7,632,646 B1 | 12/2009 | Lalvani et al. | |
| 8,496,933 B2 | 7/2013 | Paniagua-Solis et al. | |
| 2006/0024332 A1 | 2/2006 | Waters et al. | |
| 2009/0148438 A1 | 6/2009 | Nuttal et al. | |
| 2010/0015096 A1 | 1/2010 | Skeiky et al. | |
| 2010/0166786 A1 | 7/2010 | He et al. | |
| 2011/0129473 A1* | 6/2011 | Paniagua-Sol et al. | 424/135.1 |

FOREIGN PATENT DOCUMENTS

| | | |
|---|---|---|
| WO | 9324630 A1 | 12/1993 |
| WO | 2011056056 A2 | 5/2011 |

OTHER PUBLICATIONS

Stramer et al. 2009 (Emerging infectious disease agents and their potential threat to transfusion safety; Transfusion 49, August Supplement, S1-S29).*
Lopez-Valencia et al., Field Evaluation of the Protective Efficacy of *Mycobacterium bovis* BCG Vaccine Against Bovine Tuberculosis, Research in Veterinary Science, vol. 88, Issue 1, Feb. 2010, p. 44-49.
OIE (World Organization for Animal Health), Bovine Tuberculosis, 2009. Available at: http://www.oie.int/fileadmin/Home/fr/Health_standards/tahm/2.04.07_BOVINE_TB.pdf [Accessed Apr. 12, 2010].
Mexican Official Standard NOM-031-ZOO-1995, Ministry of Agriculture, Livestock and Rural Development, National Campaign Against Bovine Tuberculosis (*Mycobacterium bovis*).
Perez-Guerro et al., Epidemiologia molecular de las tuberculosis bovina y humana en una zona endemica de Queretaro, Mexico, salud publica de Mexica, vol. 50, No. 4, 2008.
Toledo-Ordonez et al., Aislamiento e identificacion de *Mycobacterium bovis* a partir de muestras de expectoracion de pacientes humanos con pacienets con problemas de respiratorios cronicos (Isolation and Identification of *Mycobacterium bovis* from sputum samples from human patients with chronic breathing problems), Veterinaria Mexico, vol. 30, No. 3, Jul.-Sep. 1999, p. 227-229.
Senasica (Servicio Nacional de Sanidad, Inocuidad y Calidad Agroalimentaria) (National Service for Health, Food Safety and Agroalimentary Quality) Tuberculosis bovina, situación actual 2011. (Bovine Tuberculosis, actual situation 2011). Available at: http://www.senasica.gob.mx/?id=4369 [Accessed Oct. 15, 2011].

(Continued)

*Primary Examiner* — Gary Nickol
*Assistant Examiner* — Mary Lyons
(74) *Attorney, Agent, or Firm* — The Webb Law Firm

(57) ABSTRACT

The invention relates to an isolated or recombinant protein from the shark *Heterodontus francisci*, which has bovine-erythrocyte-recognition activity and which can bind to sequences of antigens and/or proteins that are characteristic of infectious diseases. Once the aforementioned protein is bound to specific antigens of infectious diseases, it can haemagglutinate upon recognizing the bovine erythrocytes and antibodies characteristic of said diseases, which are present in the active state in biological samples such as whole blood, plasma or serum of bovine origin. The invention also relates to methods for protecting the detection of antibodies characteristic of infectious diseases, using the purified periplasmic extract or fusion protein, optionally purifying the recombinant protein.

**8

(56) References Cited

OTHER PUBLICATIONS

Figure 1:
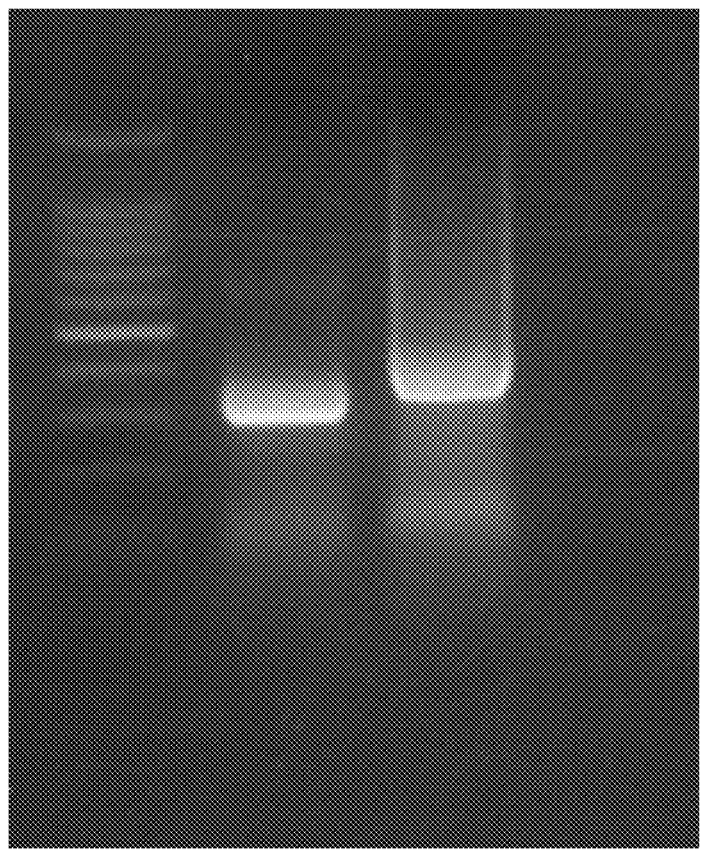
Figure 2:
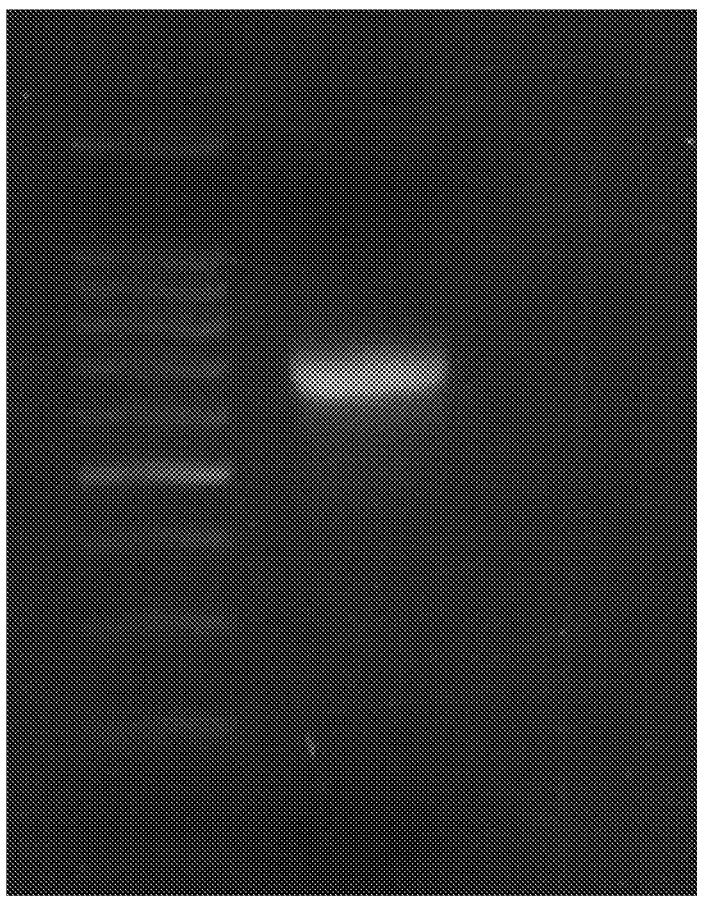

Ritacco et al., Reciprocal Cellular and Humoral Immune Response in Bovine Tuberculosis, Research in Veterinary Science, vol. 50, Issue 3, May 1991, p. 365-367.
Patarroyo et al., *Mycobacterium tuberculosis* ESAT-6 antigen inmunogenicity in Owl Monkeys. NOVA ISSN 1794-2470, vol. 4, No. 5, 2006.
Shohet et al., Erythrocite Membrane Rigidity Induced by Glycophorin A-Ligand Interaction, Journal of Clinical Investigation, vol. 75, Jun. 1985, p. 1919-1926.

Barbas et al. Phage display: a laboratory manual, EUA, New York: Cold Spring Harbor Laboratory Press, 2001.

Juarez et al., Monoclonal Antibodies for the Identification and Purification of vNAR Domains and IgNar Immunoglobulins from the Horn Shark Heterodoutus fraucisci, Hybridoma vol. 30, No. 4, 2011, pp. 323-329.

* cited by examiner

DIAGNOSTIC TEST FOR INFECTIOUS DISEASES IN CATTLE

CROSS-REFERENCE TO RELATED APPLICATIONS

This application is the United States national phase of International Application No. PCT/MX2013/000025 filed Feb. 21, 2013, and claims priority to Mexican Patent Application No. MX/a/2012/003180 filed Feb. 24, 2012, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 145514_ST25.txt. The size of the text file is 1,930 bytes, and the text file was created on Aug. 25, 2014.

TECHNICAL FIELD OF THE INVENTION

The present invention relates to the technical field of veterinary and biotechnology, more specifically it relates to the detection of antibodies typical of infectious diseases through a reaction of hemagglutination; since it provides an isolated or recombinant protein derived from shark *Heterodontus francisci*, a fusion protein containing said protein and a method for detecting antibodies to infectious diseases.

BACKGROUND

To date there are a lot of drugs and vaccines for various infectious diseases of cattle, but in some cases are not as effective if the disease is in an advanced stage. Millions of dollars are spent on research, which is mostly aimed at finding an effective treatment, downplaying the timely detection of the disease through a good method, which in many cases can lead to appropriate treatment with excellent results and offer a control on these diseases (1).

Parallel to that investment, statistics showing areas in which diseases such as bovine tuberculosis and brucellosis have not been eradicated have not decreased significantly, representing a major public health problem because they are considered zoonotic diseases (OIE, 2004) (NOM-031-ZOO-1995). (2,3)

In Mexico, the 83.11% of the country is in the process of eradication of bovine tuberculosis with a prevalence less than 0.50%, the rest of the country has a prevalence of less than 2.05%. As for brucellosis, it has been eradicated only in the state of Sonora, but in the rest of the country it has not been possible (SENASICA, 2011). Upon controlling and eradicating bovine tuberculosis a potential source for human infection will be eliminated and this has been demonstrated in several countries through campaigns of prevention, control and eradication of tuberculosis (NOM-031-ZOO-1995).

Each year, hundreds of millions of animals are slaughtered in the world because they are infected by these pathogens, causing great economic losses to livestock (NOM-031-ZOO-1995). The existing problem for both is the lack of early detection, which would allow a best control over the disease. This lack of detection in the case of brucellosis is because an unequivocal diagnosis can only be made by isolation and identification of *Brucella*, but in situations where bacteriological analysis is not possible, the diagnosis can be based on serological methods. There is no single test that allows to identify the disease, and normally a combination of growth characteristics and bacteriological and serological methods is required to determine whether the animal is infected (OIE, 2004). In the case of bovine tuberculosis, there is no clinical evidence of the disease in cattle until they have developed very extensive lesions. The measures implemented by the government are reflected in the rigorous application of the tuberculin test and the selection of cattle with positive reaction, measures that have not been very effective to date, so in general have been unsuccessful (OIE, 2004).

Moreover, other factors also influence the non timely detection of infectious diseases in cattle, such as the level of development, the quality of health systems, and access to accurate and cost-effective means of diagnosis in each country. The majority of developing countries, which lead the statistics of these diseases, have this problem. However, although some countries with economic potential have new technologies, including some commercially available for detection of the disease, they are expensive and inaccessible for most of livestock farmers. Also, diagnosis is usually reached when the damage is irreversible (OIE, 2004). Therefore, the need to create products that are sensitive to detect diseases even without clinical signs and at any stage of the disease is a priority. In that sense, the diagnostic methods used until today can be effective, but require careful sample preparation, trained staff, and especially are time consuming. Other methods that can be considered fast are not very accurate and the results are not reliable.

The classic test to detect bovine tuberculosis is the tuberculin, one of the problems of this test is that it does not detect animals without delayed-type hypersensitivity (DTH) to *Mycobacterium bovis*, termed anergic, either with a disseminated infection or a recent infection, because in such cases the cellular immunity is depressed or in development (Ritacco, 1991). On the other hand, they are laboratory tests of blood, such as lymphocyte proliferation test, the interferon gamma and enzyme immunoassay. The logistics and performing of these tests in the laboratory may be a limiting factor, thus more comparative studies of these new tests and skin tests in different field conditions are needed (OIE, 2004). Another disadvantage of tuberculin is that has a high number of false positives, because it is used a protein extract that induces cross-reactivity with non-pathogenic mycobacteria.

Works published such as Patarroyo et al. support the use of *Mycobacterium* antigens like ESAT-6 for tuberculosis detection, as it has been shown that this antigen can detect active or latent *Mycobacterium*. In this sense, the document US20060024332A1, teaches the use of a fusion protein, consisting of recombinant antigens like ESAT-6 to stimulate leucocytes and producing gamma interferon. It is considered a specific and sensitive method, but in economic terms the cost is very high and impractical. Other published works, such as US20100166786A1, US20100015096A1, US006982085B2 and US7261897B2 show the use of fusion proteins, consisting of at least two antigens of tuberculosis, and although they have the function of detecting tuberculosis, its main objective is directed to be used as preventive vaccines and also require specialized equipment and that raises the cost of the product, besides being directed to humans so far.

The detection of brucellosis is made by tests with buffered *Brucella* antigen (rose bengal) and the buffered plate agglutination test, as well as complement fixation test, enzyme-linked immunosorbent assay (ELISA) or fluorescence polarization assay. Despite they can be used to screen herds and individual animals, is a fact that no single serological test is suitable for each and every one of the epidemiological situations. Therefore, the reactivity of the samples that are positive in screening tests should be confirmed using a confirmatory strategy established. The indirect ELISA or the milk ring test, made with whole milk samples, are effective for analyzing and controlling brucellosis in dairy cows, but the milk ring test is less reliable in large herds. Another immunological test is the Brucellin skin test, which is used in analysis or as a confirmatory test in positive herds (OIE, 2004).

To a large extent several diagnostic tests for tuberculosis and brucellosis have been disclosed, which characterize by possessing antigens characteristic of the disease, or antigens that may be merged with another protein that can detect the disease, despite they mainly are used as vaccines. Although some have high sensitivity and specificity according to the investigations reported, U.S. Pat. No. 7,632,646B1 or US20100166786A1 have the disadvantages of being uneconomical, impractical and most can hardly be used in non-urban areas, causing a large consumption of transportation time, equipment and personnel training.

In order to provide a product that suppresses these drawbacks also have been created diagnostic tests that involve fusion or recombinant proteins, which are characterized by having a protein that recognizes proteins of bovine erythrocytes and other protein that detects antigens or antibodies characteristic of an infectious disease, producing a hemagglutination reaction (Shohet et al. 1985). In this sense, for some time now are available works such as WO9324630 and U.S. Pat. No. 7,585,508B1 that are clear examples of this type of recombinant proteins used in erythrocyte protein recognition by one of its proteins. In the first study, a malaria peptide is identified, and in the second a monoclonal antibody from a hybridoma; the latter shows that by merging with disease-specific antigens they produce a hemagglutination reaction, with a sensitivity of 100%. However, the use of larger volumes and concentrations is mentioned for recognizing erythrocyte protein than the protein that is the object of this invention, which has a sensitivity in the range of 90-100%, with a single addition of protein, which makes it more convenient, fast and efficient than previous ones.

This invention proposes a protein from shark *Heterodontus francisci*, which recognizes bovine erythrocyte membrane proteins and furthermore can be fused with proteins such as ESAT-6, and infectious diseases, such as tuberculosis and brucellosis. The recombinant protein can detect the disease, recognizing bovine erythrocytes and antibodies produced by the disease through a hemagglutination reaction.

Therefore, the invention disclosed herein is a good alternative to detect antibodies that may be present in infectious diseases of livestock, which will make the process very fast and that can be detected in cattle that present no symptoms and with infection in active state. Another advantage of this invention to be protected is that the costs of training personnel and logistical issues can be eliminated. Also is not limited to required concentrations of the *bacillus* to get a result, what happens to other diagnostic tests that are also impractical in rural areas.

Object of the Invention

The present invention aims to provide a recombinant protein from *Heterodontus francisci* shark, which recognizes bovine erythrocytes and further may be fused with antigens related to infectious diseases. The invention also encompasses the protein extract for induction of anti-bovine erythrocyte protein.

Another object of the invention is to provide a nucleic acid fragment encoding the anti-bovine erythrocyte protein of *Heterodontus francisci* shark with the amino acid sequence SEQ. ID. No. 2, wherein at least 85% of its sequence must be the same as the SEQ. ID. No. 1, to recognize bovine erythrocytes.

The invention also aims to provide a fusion protein to detect antibodies characteristic of infectious diseases, wherein said protein comprises the anti-bovine erythrocyte protein from *Heterodontus francisci*, as well as an antigen characteristic of an infectious disease.

Moreover, the invention provides a method for detecting antibodies characteristic of infectious diseases such as bovine tuberculosis and brucellosis, which comprises applying an effective amount of the fusion protein to a biological sample, wherein the result is observed through a hemagglutination reaction.

DISCLOSURE OF THE INVENTION

The characteristic details of the present invention are clearly shown in the following description and accompanying figures.

BRIEF DESCRIPTION OF THE FIGURES

FIG. 1 shows the profile of the gene encoding both anti-bovine erythrocyte protein and ESAT-6 through an agarose gel of 2%, with an approximate size of 300 bp for the gene coding for ESAT-6, located in lane 2, while in lane 3 is shown the gene encoding the anti-bovine erythrocyte protein with an approximate size of 350 bp, and in lane 1 shows the 3100 bp ladder (PROMEGA).

FIG. 2 shows the profile of the anti-bovine erythrocyte-ESAT-6 fusion protein through a 2% agarose gel, with an approximate size of 650 bp located in lane 2, while lane 1 shows the 100 bp ladder (PROMEGA).

Sequence list SEQ. ID No: 1 shows the nucleotide sequence of the gene encoding the protein of anti-bovine erythrocyte derived from *francisci Heterodontus* identified as SEQ. ID. No. 1.

Sequence list SEQ. ID No: 2 shows the amino acid sequence of the anti-bovine erythrocyte protein derived from *Heterodontus francisci* identified as SEQ. ID. No. 2.

Obtaining Fraction of Anti-Bovine Erythrocyte Protein from *Heterodontus francisci* Shark.

A non-immune library from *Heterodontus francisci* shark, which was previously developed at the Laboratory of Immunology and Toxins CICESE was used for obtaining the fragment of anti-bovine erythrocyte protein.

The non-immune library was cloned using the pComb3× vector, and its display, selection and expression in soluble form. By means of the phage display technique (Barbas, 2001), in round 4 of the non-immune library, a protein that is recognized by bovine erythrocytes was isolated. With phages obtained in that round the strain ER2537 was infected at optical density of 1 using SB medium with carbenicillin, to sow the sample in LB agar plates with carbenicillin al 100 μg/mL. Plates were incubated overnight at 37° C. From the colonies obtained, single colonies were selected to make a PCR with specific primers and amplify the gene encoding the anti-bovine erythrocyte protein under the following conditions: one cycle of 5 min at 94° C., 30 cycles of 45 s at 56° C., 30 cycles of 45 s at 72° C. and 1 cycle of 10 min at 72° C. From amplified products, the positive clone number 11, which had the gene fragment encoding the anti-bovine erythrocyte protein, SEQ. ID. No. 1, was selected to obtain the plasmid, following the directions of the Qiagen miniprep kit (QIAGEN) which was sent to sequencing.

Expression of the Anti-Bovine Erythrocytes Protein from *Heterodontus francisci*.

Electroporation.

Once isolated the plasmid, 5 µL were incubated on ice for 1 min, then 50 µL of electrocompetent BL21 (DE3) cells were added, and incubated on ice for 1 min. Subsequently, the mixture was poured into a cuvette for carrying out the electroporation, following the conditions 2.5 kv, 200Ω for 4 ms. Cuvette was washed with 1 mL of SOC medium, followed by two washes with 2 mL of SOC medium at a temperature range of 24 to 30° C., and was incubated for 1 hr at 37° C. at 250 rpm. 10 µL of that product of electroporation were seeded on LB plates with 100 g/mL of carbenicillin in order to isolate clones.

Induction and Protein Extraction of Anti-Bovine Erythrocytes from *H. Francisci*.

One of the clones isolated in the previous section was used to induce secretion of the anti-bovine erythrocyte protein inoculating it in LB medium containing 100 µg/L of carbenicillin and adding IPTG (1 mM), incubating for 5 hours at 37° C. Subsequently, the culture was centrifuged at 4,000×g for 20 min, and the cell packet was resuspended in 5 mL of Solution 1 (30 mM Tris-Cl, 20% sucrose, pH 8.0) and EDTA was added dropwise to a final concentration LMM and incubated in ice with stirring for 10 min. Afterwards it was centrifuged at 8,000×g for 20 min, the supernatant was recovered and the pellet was resuspended in 5 mL of Solution 2 ($MgSO_4$ 5 mM), which was incubated on ice with stirring for 20 min and was centrifuged again at 8,000×g for 20 min, and the supernatant was recovered. The protein present in the supernatant obtained by using Solution 2 for enzyme-linked immunoassay (ELISA) was used to observe its expression.

Hemagglutination Assays.

To demonstrate that the anti-bovine erythrocyte protein exhibited a hemagglutination reaction being in contact with bovine erythrocytes, in vitro assays were performed on culture plates with blood samples from cattle.

Prior to conducting the tests, a sample of 5 mL of bovine peripheral blood was obtained via venipuncture. Serum sample is separated from cellular package and the package is washed 3 times with 1×PBS solution and resuspended in 10 mL of the same solution to use it later as a solution of washed erythrocytes. In the tests induction extract purified was used and quantified to a concentration of 10 µg/mL.

The test consisted of adding to each well in triplicate, 30 µL of washed erythrocytes solution; then was added the extract of anti-bovine erythrocyte protein in a volume range of 10-80 µL, allowing to stand for 30 min. Alfalfa sprouts were used as positive control, and PBS1× as negative control. Table 1 shows the effect of isolated protein from *Heterodontus francisci* on bovine erythrocytes, where can be seen that the effect of hemagglutination is positive, which represents that the invention can be used with effective results.

TABLE 1

Recognition of bovine erythrocytes by the anti-bovine erythrocyte protein in different amounts through a reaction of hemagglutination.

| Sample | 10 µL | 20 µL | 30 µL | 40 µL | 60 µL | 80 µL |
|---|---|---|---|---|---|---|
| Bovine erythrocytes | ++ | ++ | +++ | +++ | +++ | +++ |

Agglutination: +
No agglutination: −

Obtaining Overlapping Anti-Bovine Erythrocyte Protein~Antigen.

From the results shown above, the anti-bovine erythrocyte protein isolated from *H. francisci* shark demonstrates its great ability to recognize erythrocytes through a hemagglutination reaction. Thus, by fusing the anti-bovine erythrocyte protein with antigens from bacteria, viruses or fungi which may cause diseases such as tuberculosis, brucellosis, rabies, among others, the pathology can be detected by the hemagglutination reaction through the recognition of erythrocytes and also the antibodies to the disease, considering this invention so far, fast, effective and practical compared to those currently used.

For Detection of Bovine Tuberculosis, Anti-Bovine Erythrocytes—eSAT-6.

To detect bovine tuberculosis, ESAT-6 antigen was used. The gene of both proteins, bovine erythrocytes and anti-ESAT-6 is used.

We proceeded to overlap them using a PCR reaction with ramp, under the following conditions: 1 cycle of 5 min at 94° C., 5 cycles of 45 s at 94° C., 5 cycles of 16.5 min starting with 50° C. and an increase of 1° C. every 45 s, followed by 25 cycles of 12.75 min at 55° C. with an increase of 1° C. every 45 s, 1 cycle of 45 s at 72° C. and finally 1 cycle of 10 min at 72° C. With the chimeric gene of anti-bovine erythrocytes and ESAT-6, it was digested with SfiI enzyme like the pComb3× vector, so that sticky ends were ligated, precipitating the product of digestion with 1 µL glycogen, 20 µL acetate 3M sodium and 70% ethanol, incubating for 2 hrs at −70° C. The mixture was centrifuged at 16,000×g for 30 minutes, the pellet was resuspended in 20 µL of nuclease-free water and quantitated for subsequent ligation with T4 ligase enzyme (Promega). Then it is proceeded to electroporate into electrocompetent BL21 (DE3) cells and the product is seeded in LB agar plates with carbenicillin 100 µg/mL. Secretion of the protein is induced in positive clone by adding IPTG (1 mM Promega) and incubating for 5 hours at 37° C. The protein extraction was performed as described in "Induction, protein extraction and anti-bovine erythrocytes from *H. francisci*". The ability to express the anti-bovine erythrocyte-ESAT-6 fusion protein is measured by reading an enzyme-linked immunoassay comprising: Plate the protein in triplicate and incubating for one hour at 37° C. Discard the content and block wells with BSA3%-PBSI, incubating for one hour at 37° C. The wells are washed with 0.05% Tween-PBS1× three times, added 50 µL of mouse monoclonal antibody anti-HA (ROCHE) diluted 1:1000 in 1% BSA-PBS1× incubating 1 hr at 37° C. It is washed with 0.05% Tween-PBS1× three times and 50 µL of peroxidase substrate are added, consisting of 20 µg/mL ABTS, 1× citrate buffer, 0.3% hydrogen peroxide, allowing to stand for 20 min without light stimulus. In FIG. 2, the profile presented by overlapping of such anti-bovine erythrocyte-ESAT-6 fusion protein is shown.

Hemagglutination Assays with Fusion Protein.

In order to demonstrate that the fusion protein (anti-bovine erythrocyte protein-antigen) has the same ability to hemagglutinate bovine than the bovine erythrocyte protein unfused by recognizing antibodies to infectious diseases, hemagglutination tests were performed with the fusion protein. Periplasmic extract of the fusion protein was used.

The procedure was the same as the hemagglutination assays outlined above for anti-erythrocyte protein, with the only difference that they had contacted an experimental sample. The only variations in methodology were in the case of whole blood.

Example 1

Effect of Anti-Bovine Erythrocyte-ESAT-6 Fusion Protein in Bovine Serum Samples To verify the functionality of the anti-bovine erythrocyte-ESAT-6 fusion protein, samples of cattle with tuberculosis confirmed by other conventional methods, like the acid fast bacilli (AFB) and culture (gold standard), which even when shown to be reliable and safe tests, for diagnosis of tuberculosis, involve undue cost and time compared to this invention. The samples were subjected to the following methodology: were taken 25 μL total bovine blood, which was centrifuged at 750×g for 3 min and the cell package was washed with PBS1×. After completing the washing process, again the erythrocytes were centrifuged, the supernatant was discarded and the erythrocytes were resuspended in 20 μL of experimental serum. 25 μL of anti-bovine erythrocyte-ESAT 6 fusion protein was added, and allowed to incubate at room temperature for 30 min. Alfalfa sprouts were used as a positive control, and as negative control PBS1×.

Table 2 shows that in the samples occurred hemagglutination with an effectiveness of 100% for the fusion protein, the same as a conventional method, however, the advantage of using the anti-bovine erythrocyte-ESAT-6 fusion protein is observed in the ability to detect the antibodies produced by the tuberculosis effectively and quickly, representing savings in time, expenses, supplies and infrastructure for the health sector.

TABLE 2

Percentage of sensitivity of samples with TB confirmed exhibiting hemagglutination using conventional methods such as AFB and culture, and using antiglycophorin-ESAT-6 purified fusion protein.

| Samples | AFB and culture Conventional method | Anti-bovine erythrocytes - ESAT fusion protein |
|---|---|---|
| Bovine sera | 100% | 100% |

By the above result, it can be implemented as a new technique to detect infectious diseases such as tuberculosis, as anti-erythrocyte-ESAT-6 fusion protein can detect antibodies in active or latent form by a hemagglutination reaction.

Example 2

Effect of Anti-Bovine Erythrocyte-ESAT-6 Fusion Protein in Whole Blood from Cattle The anti-bovine erythrocyte-ESAT-6 fusion protein not only has the ability to be used on infected bovine serum samples, but can also be used on whole blood samples and have the same effect and sensitivity. This saves even more time and a quantity as large of sample is not required, as only uses 3 to 5 drops of blood. Drops of blood are diluted in PBS 1×. In a watch glass 500 μL of the sample and 10 μL of the fusion protein are placed with stirring, and after 15 minutes the result is interpreted. Table 3 shows that 30 samples with tuberculosis confirmed previously by a conventional method have a sensitivity of 100% for tuberculosis antibody detection when antiglycophorin-ESAT-6 purified fusion protein is used.

TABLE 3

Percentage of sensitivity of whole blood samples, with tuberculosis confirmed by a conventional method and with the antiglycophorin-ESAT-6 purified protein.

| Samples | AFB and culture Conventional method | Antiglycophorin ESAT-6 purified fusion protein |
|---|---|---|
| 30 whole blood | 100% | 100% |

Given the above, the anti-bovine erythrocyte protein from *Heterodontus francisci* shark is novel because it has the property of recognizing erythrocytes of cattle in samples of whole blood or serum, and also has the ability to fuse with infectious diseases antigens, recognizing antibodies of the same via a hemagglutination reaction.

REFERENCES

1. Field Evaluation of the protective efficacy of *Mycobacterium bovis* BCG vaccine against bovine tuberculosis. C. López Valencia, T. Rentería Evangelista, J. de Jesús Williams, A. Licea Navarro, A. De la Mora Valle, G. Medina Basaltos.
2. Epidemiología molecular de las tuberculosis bovina y humana en una zona endémica de Querétaro, Mexico. (Molecular epidemiology of bovine and human tuberculosis in an endemic area of Querétaro, Mexico). M C Laura Pérez-Guerrero, M V Z MSc, PhD Feliciano Millán-Suazo, Q, MSc, PhD Camila Arriaga-Díaz, M V Z Cecilia Romero-Torres, M C Minerva Escartín-Chávez. Approved on Jan. 17, 2008.
3. Aislamiento e identificación de *Mycobacterium bovis* a partir de muestras de expectoración de pacientes humanos con pacienets con problemas de respiración crónicos. (Isolation and Identification of *Mycobacterium bovis* from sputum samples from human patients with patients with chronic breathing problems). Paola Toledo Ordóñez, Feliciano Milian Sauzo, Marco Antonio Santillán Flores, Isaura Carolina Ramírez Caslla. Accepted on Feb. 22, 1999.
4. Reciprocal cellular and humoral immune Response in bovine tuberculosis. RITACCA V, Lopez B, Cantor I N, Barrera I, Errico F, Nader. Res. Vet. Sci. 1991; 50: 365-367.
5. Mexican Official Standard NOM-031-ZOO-1995, Ministry of Agriculture, Livestock and Rural Development, National Campaign against Bovine Tuberculosis (*Mycobacterium bovis*).
6. OIE-World Organization for Animal Health, 2004.
7. Sagarpa, SENASICA, 2011.

Having sufficiently described the invention, it is considered as a novelty and therefore claimed as proprietary what is contained in the follow clauses:

1. A fusion protein comprising:
   a) a protein comprising the sequence SEQ ID NO: 2; and
   b) an infectious disease antigen, wherein the infectious disease antigen comprises a protein.

2. A composition comprising the fusion protein of claim 1 and a saline solution.

3. An in vitro method for detecting antibodies to infectious diseases comprising the steps of:
   a) contacting a biological sample from cattle with the fusion protein of claim 1; and
   b) detecting the presence of antibodies associated with infectious diseases in the biological sample, using bovine erythrocyte agglutination,
   wherein the infectious disease is one or more of tuberculosis, brucellosis, and rabies.

4. The method according to claim 3, wherein the biological sample is derived from a subject under study.

5. The method according to claim 3, wherein the biological sample comprises whole blood, plasma or serum derived from blood.

6. The method according to claim 3, wherein the infectious disease is tuberculosis.

7. The method according to claim 3, wherein the infectious disease is brucellosis.

8. The method according to claim 3, wherein the infectious disease is rabies.

* * * * *

SEQUENCE LISTING

```
<160> NUMBER OF SEQ ID NOS: 2

<210> SEQ ID NO 1
<211> LENGTH: 326
<212> TYPE: DNA
<213> ORGANISM: Heterodontus francisci
```

```
<400> SEQUENCE: 1
tggccgcaag ggtggcccaa acaccttcaa cggcaacgag agagacaggc gaatccctga    60
ccgttaactg cgtcctcgtt gatgctgagt atggtttata cagcacgtct tggtaccgca   120
gtaatccggg ttcaacagac agggaacaca taacgattgg cggacgatat gttgaatcag   180
tcaacaaagg agcaaagtca tttctctgc  aaatcaagga catgacagtt gaagacagtg   240
gcagatatta ctgcaacgcg cgagcggaga tatctcaagg acatacgcgc tcctacatcg   300
gagctggcac cgtgctgact gtgaac                                         326

<210> SEQ ID NO 2
<211> LENGTH: 108
<212> TYPE: PRT
<213> ORGANISM: Heterodontus francisci

<400> SEQUENCE: 2

Ala Ala Arg Val Ala Gln Thr Pro Ser Thr Ala Thr Arg Glu Thr Gly
1               5                   10                  15

Glu Ser Leu Thr Val Asn Cys Val Leu Val Asp Ala Glu Tyr Gly Leu
                20                  25                  30

Tyr Ser Thr Ser Trp Tyr Arg Ser Asn Pro Gly Ser Thr Asp Arg Glu
            35                  40                  45

His Ile Thr Ile Gly Gly Arg Tyr Val Glu Ser Val Asn Lys Gly Ala
        50                  55                  60

Lys Ser Phe Ser Leu Gln Ile Lys Asp Met Thr Val Glu Asp Ser Gly
65                  70                  75                  80

Arg Tyr Tyr Cys Asn Ala Arg Ala Glu Ile Ser Gln Gly His Thr Arg
                85                  90                  95

Ser Tyr Ile Gly Ala Gly Thr Val Leu Thr Val Asn
            100                 105
```